(12) United States Patent
Hazen et al.

(10) Patent No.: US 6,871,169 B1
(45) Date of Patent: Mar. 22, 2005

(54) COMBINATIVE MULTIVARIATE CALIBRATION THAT ENHANCES PREDICTION ABILITY THROUGH REMOVAL OF OVER-MODELED REGIONS

(75) Inventors: Kevin H. Hazen, Phoenix, AZ (US); Suresh Thennadil, Tempe, AZ (US); Timothy L. Ruchti, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 738 days.

(21) Appl. No.: 09/630,201

(22) Filed: Aug. 1, 2000

Related U.S. Application Data (63) Continuation-in-part of application No. 09/610,789, filed on Jul. 6, 2000, now abandoned, which is a continuation-in-part of application No. 08/911,588, filed on Aug. 14, 1997, now Pat. No. 6,115,673.

(51) Int. Cl.[7] ............ G06F 7/60; G06F 17/10; G06F 101/00
(52) U.S. Cl. ............ 703/2; 703/12; 702/22; 356/39
(58) Field of Search ............ 703/2, 12; 702/22–32; 356/39

(56) References Cited

U.S. PATENT DOCUMENTS

| | | | |
|---|---|---|---|
| 5,252,829 A | 10/1993 | Nygaard et al. | 250/339 |
| 5,379,764 A | 1/1995 | Barnes et al. | 128/633 |
| 6,040,578 A | 3/2000 | Malin et al. | 250/339.12 |
| 6,115,673 A * | 9/2000 | Malin et al. | 702/23 |
| 6,219,132 B1 * | 4/2001 | Scharlack et al. | 356/39 |
| 6,341,257 B1 * | 1/2002 | Haaland | 702/27 |

OTHER PUBLICATIONS

Mark et al, "Linearity in Calibration —Act II, Scene, II," Spectroscopy, vol. 14 No. 1, pp. 16–17 (Jan. 1999).*

* cited by examiner

Primary Examiner—Samuel Broda
(74) Attorney, Agent, or Firm—Glenn Patent Group; Michael A. Glenn (57) ABSTRACT

A novel multivariate model for analysis of absorbance spectra allows for each wavelength or spectral region to be modeled with just enough factors to fully model the analytical signal without the incorporation of noise by using excess factors. Each wavelength or spectral region is modeled utilizing its own number of factors independently of other wavelengths or spectral regions. An iterative combinative PCR algorithm allows a different number of factors to be applied to different wavelengths. In an exemplary embodiment, a three-factor model is applied over a given spectral region. The residual of the three-factor model is calculated and used as the input for an additional five-factor model. Prior to the additional five factors being applied, some of the wavelengths are removed. This leads to a three-factor model over the first region and an eight-factor model over the second region. This analysis of residuals can be repeated such that a one to n factor model could be applied to any given wavelength, or rather any number of factors may be employed to model any given frequency or spectral region. A method of predicting concentration of a target analyte from sample spectra applies a calibration developed using the inventive PCR algorithm to a matrix of sample spectral to generate a vector of predicted concentrations for the target analyte.

46 Claims, 7 Drawing Sheets

COMBINATIVE MULTIVARIATE CALIBRATION THAT ENHANCES PREDICTION ABILITY THROUGH REMOVAL OF OVER-MODELED REGIONS

CROSS REFERENCE TO RELATED APPLICATIONS

This application is a Continuation-in-part of U.S. patent application Ser. No. 09/610,789, filed Jul. 6, 2000, abandoned, which is a Continuation-in-part of U.S. patent application Ser. No. 08/911,588, filed on August 14, 1997, now U.S. Pat. No. 6,115,673.

BACKGROUND OF THE INVENTION

1. Field of the Invention

The invention relates to multivariate analysis of spectral signals. More particularly, the invention relates to a method of multivariate analysis of: a spectral signal that allows for a wavelength or spectral region to be modeled with just enough factors to fully model the analytical signal without the incorporation into the model of noise by using excess factors.

2. Description of Related Art

Multivariate analysis is a well-established tool for extracting a spectroscopic signal, usually quite small, of a target analyte from a data matrix in the presence of noise, instrument variations, environmental effects and interfering components. Various methods and devices have been described that employ multivariate analysis to determine an analyte signal. For example, R. Barnes, J. Brasch, D. Purdy, W. Loughheed, Non-invasive determination of analyte concentration in body of mammals, U.S. Pat. No. 5,379,764 (Jan. 10, 1995) describe a method in which a subject is irradiated with NIR (near-IR) radiation, a resulting absorption spectrum is analyzed using multivariate techniques to obtain a value for analyte concentration.

J. Ivaldi, D. Tracy, R. Hoult, R. Spragg, Method and apparatus for comparing spectra U.S. Pat. No. 5,308,982 (May 3, 1994) describe a method and apparatus in which a matrix model is derived from the measured spectrum of an analyte and interferents. A spectrum is generated for an unknown sample. Multiple linear least squares regression is then utilized to fit the model to the sample spectrum and compute a concentration for the analyte in the sample spectrum.

L. Nygaard, T. Lapp, B. Arnvidarson, Method of determining urea in milk, U.S. Pat. No. 5,252,829 (Oct. 12, 1993) describe a method and apparatus for measuring the concentration of urea in a milk sample using an infrared attenuation measuring technique. Multivariate techniques are carried to determine spectral contributions of known components using partial least square algorithms, principal component regression, multiple linear regression or artificial neural network learning.

M. Robinson, K. Ward, R. Eaton, D. Haaland, Method of and apparatus for determining the similarity of a biological analyte from a model constructed from known biological fluids, U.S. Pat. No. 4,975,581 (Dec. 4, 1990) describe a method and apparatus for determining analyte concentration in a biological sample based on a comparison of infrared energy absorption between a known analyte concentration and a sample. The comparison is performed using partial least squares analysis or other multivariate techniques.

However, multivariate techniques such as principal component regression (PCR) and partial least squares regression (PLS) have some inherent disadvantages. One well-documented problem with multivariate analysis is that noise in the data may be incorporated into the model. This is especially true when too many factors are employed in the development of the model. The modeling of this noise results in subsequent prediction matrices with erroneously high error levels. See, for example, H. Martens, T. Naes, *Multivariate Calibration* John Wiley & Sons, 1989; or K. Beebe, B. Kowalski, *An Introduction to Multivariate Calibration and Analysis Anal. Chem.* 59, 1007A–1017A (1987). Complicating this issue is the fact that few factors may fully model a given spectral region, while additional factors may be required to model another set of wavelengths.

For example, a few factors may model a region having:
A. a high degree of co-linearity;
B. high signal to noise ratio;
C. minor or readily modeled instrument variations;
D. low contribution of environmental effect; or
E. a minimal number of readily modeled interfering signals.

Other regions may require a much larger number of factors in order to sufficiently model the analytical signal. This may be the case when:
A. the data are not fully linear;
B. in low signal to noise regions;
C. instrument drift changes spectral response over time;
D. a large number of spectrally interfering components are present; or,
E. interfering signals are not readily modeled.

In traditional applications of multivariate techniques such as PCR or PLS, a single number of factors is applied over an entire spectrum. This means that for a given region within the spectrum, selection of the appropriate number of spectral factors to adequately model the signal will result in all other spectral regions using the same number of factors. In many cases, another spectral region would be optimally modeled with a different number of factors than the first spectral region. Thus, a compromise between wavelength selection and the number of factors to incorporate into the model becomes necessary. There exists, therefore, a need in the art for an algorithm that allows the number of factors for each wavelength or spectral region to be chosen independently of the number of factors utilized to model a different wavelength or spectral region.

SUMMARY OF THE INVENTION

The invention provides a combinative PCR algorithm that allows a different number of factors to be applied to different wavelengths or spectral regions during modeling of a matrix of calibration spectra. In an exemplary embodiment, a three-factor model is applied over a given spectral region, wherein concentrations of a target analyte are known. The residual of the three-factor model is calculated and used as the input for an additional five-factor model. Prior to the additional five factors being applied, some of the wavelengths are removed, with the result that a three-factor model is applied over the first spectral region and an eight-factor model over the second region. This analysis of residuals may be repeated such that a one to n factor model may be applied to any given wavelength or rather any number of factors may be employed to model any given frequency. The scores matrices of the individual models are concatenated to arrive at a final scores matrix for the entire calibration matrix. Principal component regression is employed to regress the calibration matrix against the vector of analyte concentrations to derive a calibration model, the model comprising a vector of calibration coefficients.

A method of predicting concentrations of a target analyte from a prediction data set composed of a matrix of sample spectra applies the above calibration to a final scores matrix for the sample matrix to generate a vector of predicted values for target analyte concentration. The sample matrix is iteratively modeled in the same fashion as the calibration matrix, with the final scores matrix being a concatenation of the individual scores matrices for the various spectral regions or wavelengths. The vector of coefficients from the calibration data set in combination with the scores from the prediction the prediction data is used to generate this vector of analyte concentrations.

DETAILED DESCRIPTION

The invention provides a combinative PCR (Principal Component Regression) algorithm that allows for each wavelength or spectral region of a spectral signal to be modeled with just enough factors to fully model the analytical signal without the incorporation in the model of noise by using excess factors. Each wavelength or spectral region may utilize its own number of factors independently of other wavelengths or spectral regions. A novel multivariate model incorporating the invented algorithm is also provided.

The combinative PCR algorithm allows a different number of factors to be applied to different wavelengths, or regions, of a spectral signal. In the exemplary embodiment of the invention that follows, a three-factor model is applied over a given spectral region. The exemplary embodiment is provided only as a description, and is not intended to be limiting. The residual of the three-factor model is calculated and used as input for a further five-factor model. However, prior to the additional five factors being applied, some of the wavelengths used for the three-factor model are removed. The removed wavelengths constitute a first spectral region. The remaining wavelengths constitute a second spectral region. Thus, a three-factor model is applied over the first region and an eight-factor model over the second region. Those skilled in the art will realize that this analysis of residuals can be repeated such that a one to u factor model may be applied to any given wavelength of spectral region. Stated another way, any number of factors may be employed to model any given frequency or spectral region.

Figure 1:
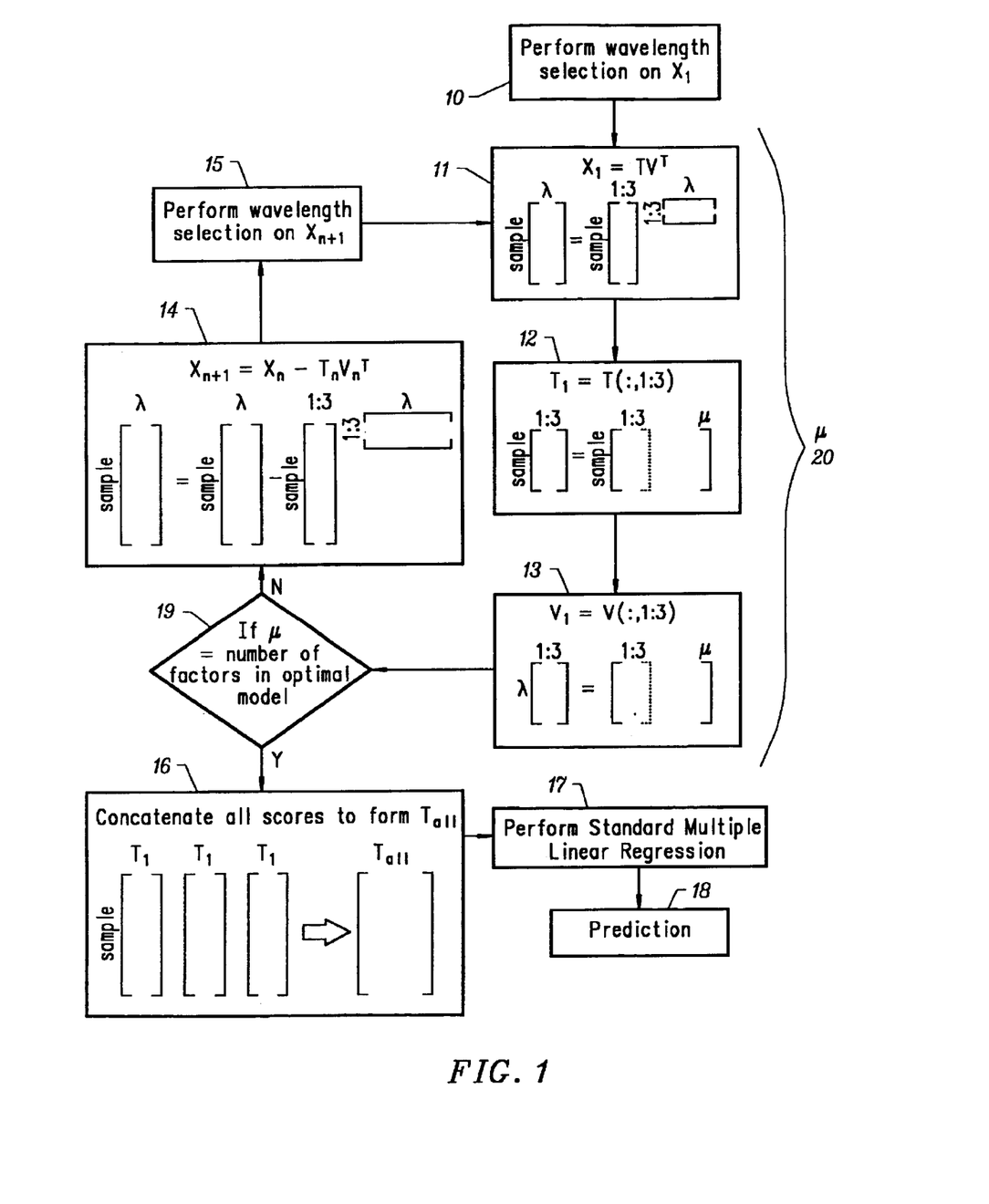
FIG. 1 is a schematic diagram of the steps of a combinative PCR algorithm, according to the invention.

Referring now to FIG. 1, a block diagram illustrating the several steps of the invented algorithm is provided. $X_1$ is a matrix of absorbance spectra comprising i samples and k variables, or in this case, wavelengths. Y is a vector of concentrations of a target analyte, where the concentrations are independently determined (i samples×1). Presented below are the several steps of the invented algorithm in overview. A detailed discussion of the algorithm follows further below. Wavelength selection is initially performed on $X_1$ (10, FIG. 1).

1. Decompose $X_1 = TV^T$ using a standard PCA function to generate a matrix of loading vectors V, followed by regression to generate a scores matrix T; (11)

2.
    a. Set $T_1 = T_u(:,1:z_n)$, where u=the number of factors in an optimal model, z=the number of factors used for an iteration and n denotes the current iteration. In the currrent embodiment, $z_1=3$, thus a selection of three factors is used for the initial spectral range, however more or fewer factors may be employed in this step; (12)
    b. Set $V_1 = V_u(:,1:z_n)$; (13)

3.
    a. Compute residual spectra $X_2 = X_1 - T_1 V_1^T$; (14)
    b. Undesirable wavelengths are removed from $X_2$ (15) Several methods of selecting the wavelengths to be removed are indicated below; following wavelength selection, $X_2$ now serves as the new input matrix.

Steps 1–3 above are repeated, as shown below:

4. Decompose $X_2 = T_1 V_1^T$ using standard chemometric techniques known to those skilled in the art; (11)

5. Set $T_2 = T_u(:,1:z_n)$ (12) and $V_2 = V_u(:,1:z_n)$ (13). In the current iteration, where n=2, $z_{2=5}$, thus five factors are used in the second spectral range for purposes of description. In actual practice, more or fewer factors could be used;

6.
    a. Compute residual spectra: $X_3 = X_2 - T_2 V_2^T$; (14) and
    b. Wavelength selection is again employed using $X_3$ as the input matrix (15).

Several approaches to wavelength selection may be utilized:

- remove noisy regions by squaring the residual and removing large value areas;
- remove regions with large noise characteristics; or
- remove regions where the raw absorbance spectra had high absorbance, since noise is related to absorbance.

The steps can be repeated as many times as are required such that $T_a$ and $V_a$ are generated, where a=the total number of iterations. As FIG. 1 shows, where u=the number of factors in an optimal model (19), steps 1–3 must go through a iterations (20) to generate $T_a$ and $V_a$;

1. The final scores matrix, $T_{all}$, is generated by concatenating all of the T's:

$$T_{all} = [T_1 T_2 T_3 \ldots T_s] \quad (16)$$

It should be noted that the loading vectors may not be concatenated, since the vectors are of different lengths.

2. Calculate calibration coefficients by performing standard multiple linear regression (17), as below:

$$y = Ts$$

$$T^T y = T^T T s$$

$$(T^T T)^{-1} T^T y = s$$

$$s = (T_T T)^{-1} T^T y;$$

where s is a vector of coefficients.

3. Predict analyte concentration: (Prediction Data Set)
   a. Compute $T'_1=X'V_1$, where $V_1$ is obtained in the calibration set;
   b. Compute the residual, $X'_1=X'-T'_1V_1^T$;
   c. perform wavelength selection utilized on calibration matrix;
   repeat sub-steps a and b as needed
   d. Compute $T'_2=)X'V_2$;
   e. Compute the residual, $X'_2=X_{1\_}'T'_2V_2^T$;
   f. Perform wavelength selection as in calibration;
   repeat until $T_a$ is reached.
   g. Concatenate all values for $T'_n$:

$$T'_{all}=[T'_1T'_2T'_3 \ldots T'_a].$$

h. Predict concentration of target analyte, $y_{pred}=(T'_{all})s$.

An alternative embodiment of the modified PCR algorithm applies PCR with a set number of factors to all spectral regions requiring that number of factors. A separate PCR model with a second number of factors may be applied to individual wavelengths or spectral regions requiring that number of factors. The process may be repeated such that one to n factors are applied for each spectral region or wavelength. Scores may be concatenated as above with calibration coefficients being generated and predictions being performed as in steps 8 and 9.

In the following example, computer simulated near-IR spectral data sets of serum are utilized to demonstrate the feasibility of the combinative PCR algorithm described above.

EXAMPLE

Phantom Serum Spectra Generation: Near-IR absorbance spectra of water, albumin, triglycerides, cholesterol, glucose and urea with a concentration of 1 g/dL at 37.0° C. and a 1 mm pathlength were generated from spectra collected on a NICOLET 860 IR Spectrometer, supplied by Nicolet Instrument Corporation of Madison Wis., in transmission mode with subsequent multivariate curve resolution analysis. The pure component spectra were used to generate phantom serum spectra by additive additions of the absorbances of the constituent components, where the concentration of each constituent was randomly selected from the concentration ranges in Table 1, below. Noise proportional to the resulting spectral absorbance at each wavelength was then added, with the standard deviation of the added noise being a percentage of the total absorbance; thus yielding spectra with increased noise levels at higher absorbance levels.

TABLE 1

Concentration Range of Constituents Used in Serum Phantom.

| Component | Concentration (mg/dL) |
|---|---|
| Water | 95,000 to 96,000 |
| Albumin | 2,000 to 8,000 |
| Triglycerides | 100 to 700 |
| Cholesterol | 120 to 400 |
| Glucose | 40 to 600 |
| Urea | 5 to 70 |

Figure 2:
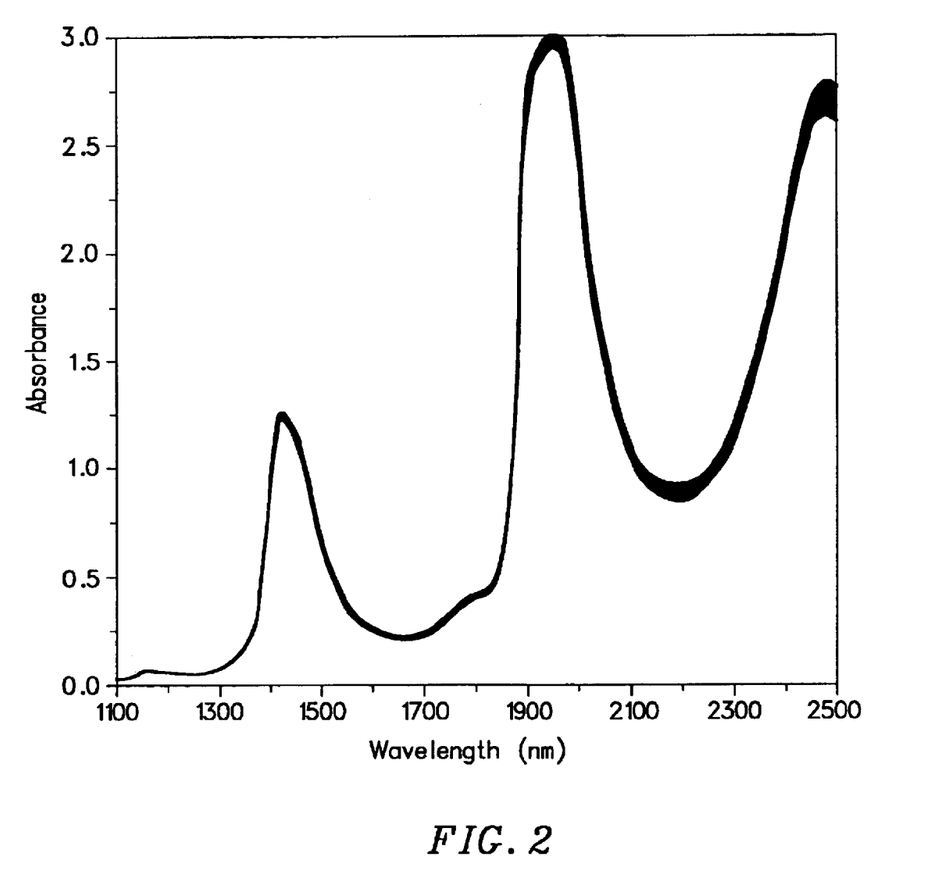
FIG. 2 shows an assortment of exemplary spectra from a set of spectra generated for a calibration data set, according to the invention.

Calibration, Monitoring and Prediction Set Generation: A total of 60 spectra were generated for a calibration data set and 20 spectra were generated for a monitoring data set utilized in the wavelength selection process. The standard deviation of the applied noise levels for the calibration, and monitoring data sets is 0.002 times the absorbance level at each wavelength. A random selection of these generated spectra is presented in FIG. 2. The well-known near-IR water absorbance bands are observed at 1450, 1950 and 2500 nm. Upon detailed inspection, some of the fat bands at 1167, 1210, 1391, 1413, 1724, 1760, 2123, 2144, 2307, 2347 and 2380 nm may be identified along with some of the protein absorbance bands at 1690, 1730, 2170 and 2285 nm. The glucose, cholesterol and urea absorbance bands are not obvious in the raw spectra.

Prediction spectra consisted of 80 independent spectra at each of 30 noise levels where one standard deviation of the noise level varied from 0.0002 to 0.006 times the absorbance. For each of these 30 noise levels, 50 sets of 80 independent spectra were generated. In no case were parameters optimized with the prediction data sets. In addition, no human feedback from the predictions was utilized in optimization of the parameters for building the model with the calibration and monitoring data sets. Results from predictions represent the first and only analysis of the data. The thirty separate standard errors of prediction (SEP) reported at noise levels from 0.0002 to 0.006 are the mean SEP's of the 50 independent prediction sets at each of the noise levels.

Calibration: For comparative purposes, the conventional PCR algorithm was utilized to analyze the generated spectral data sets. For the standard PCR algorithm, wavelength optimization through wavelength selection was performed on the calibration and monitoring data sets, with the standard error of the monitoring data set used as a metric for optimization. Wavelength optimization for the standard PCR algorithm resulted in the spectral ranges of 1100 to 1862 and 1978 to 2218 nm being selected for removal, which, as would be expected, corresponds to removal of the high water absorbance regions about 1900 and 2500 nm.

For the combinative PCR algorithm, wavelength optimization was again performed on the calibration and monitoring data sets with the standard error of prediction, of the monitoring data set used as the metric for optimization. However, using the inventive PCR algorithm, wavelength optimization was performed with each PCR iteration. In the first iteration, a total of three PCR factors were utilized with the spectral regions 1100 to 1886 and 1980 to 2378 nm. Notably, standard PCR utilized a long wavelength cutoff of 2218 nm that excluded the sharply increasing water absorbance band that leads to higher noise levels, while the first iteration of the modified PCR algorithm had a long wavelength cutoff at 2378 nm that includes more of this high noise region. Likewise, traditional PCR removed a larger region about the 1950 nm water absorbance band compared to the first iteration of the modified PCR algorithm. The modified PCR algorithm is able to incorporate these noisy regions, since only a three-factor model is utilized in these regions.

Prior to the second iteration of PCR, a new wavelength selection was performed on the residual spectra from the first PCR iteration. The mean residual of the 60 residual calibration spectra was calculated using Equation 1 where $X_1$ is the data matrix used in the initial PCR iteration and $T_1$ and $V_1$ are the scores and loadings for the initial 3-factor model:

$$Resi = \text{mean}(X_1 - T_1 V_1^T), \qquad (1)$$

Figure 3:
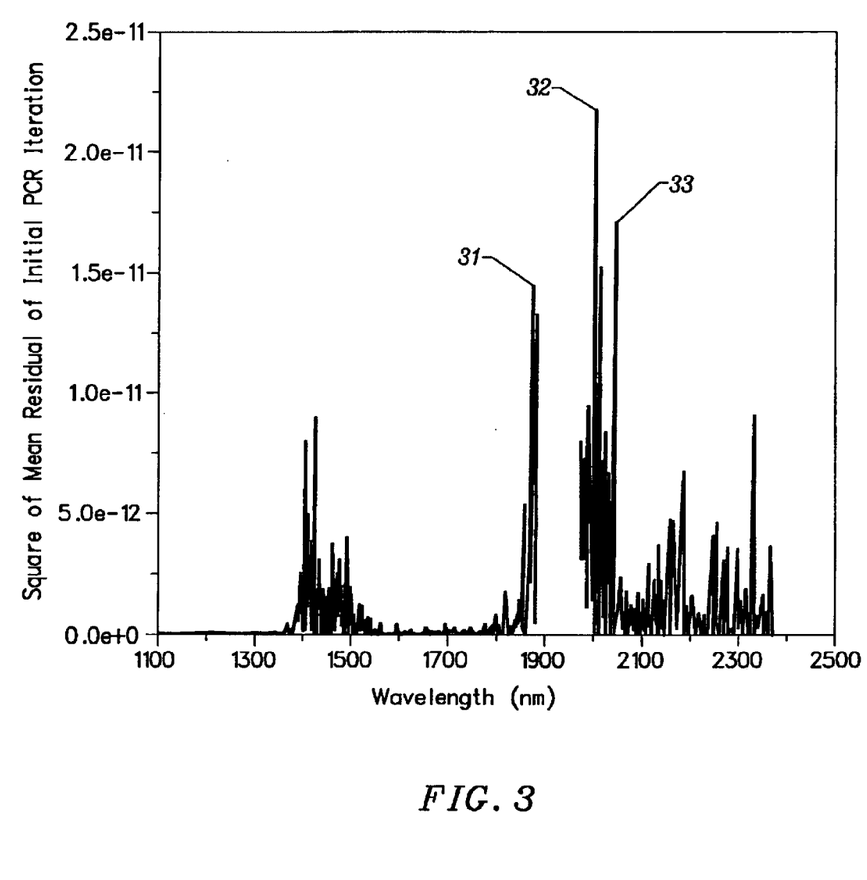
FIG. 3 provides a plot of the square of a mean residual spectrum calculated from a set of residual calibration spectra, according to the invention.
Figure 4:
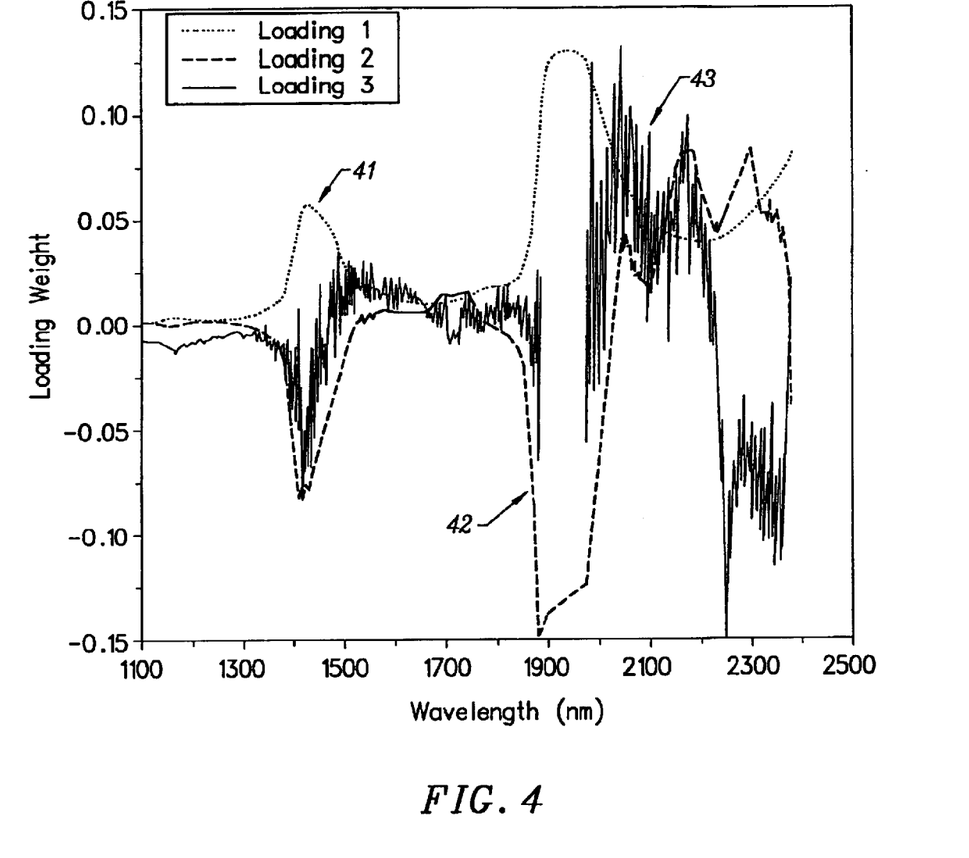
FIG. 4 shows a plot of the first three loadings from an initial PCR iteration according to the invention.

The square of the resulting mean residual spectrum is plotted in FIG. 3. In regions 31, 32, 33 where the square of the mean residual is high, noise is dominant. The large square of the residual serves as one basis for wavelength selection. The loadings provide a second basis for wavelength selection. In FIG. 4, the three spectral loadings generated in the first iteration of PCR are presented. The first loading 41 is dominated by water while the second spectral loading 42 shows considerable structure in the combination band region corresponding to protein. However, the third loading 43 shows considerable noise about 1950 and 2350 nm. After combining this loading information with the square of the mean residual information prior to the second PCR iteration, the spectral region from 1980 to 2070 nm was removed due to the high noise level, as was the region from 2280 to 2378 nm. The second PCR iteration utilized an additional four factors yielding a total of seven factors for the remaining spectral regions. Notably, the remaining spectral region continues to include the glucose absorbance band located at 2272 nm that was excluded from the traditional PCR algorithm. The standard PCR algorithm generated its optimal prediction abilities based largely upon the three glucose absorbance bands in the first overtone region from 1500 to 1800 nm. However, the first overtone includes smaller and broader absorption features that require additional factors to be properly modeled. The large number of factors required for this region, plus the limitation of a fixed number of factors for all wavelengths imposed by conventional PCR, necessitated the removal of some of the glucose containing information in the combination band region to avoid later factors adding undue amounts of noise into the model from the combination band region.

The start and stop wavelength pairs utilized in the modified PCR algorithm for each PCR iteration along with the total number of factors for each iteration is summarized in Table 2, below. Later iterations gradually widen the removal of the water absorbance bands at 1950 and 2500 nm. In addition, the entire combination band and the peak of the water absorbance band at 1450 nm are removed after the first 3 iterations.

TABLE 2

Wavelength Selection at each PCR Iteration for Calibration and Monitoring Spectra.

| PCR Iteration | Number of Factors | Spectral Range (First and Last Wavelengths in nm) |
| --- | --- | --- |
| 1 | 3 | 1100 to 1886 |
|   |   | 1980 to 2378 |
| 2 | 4 | 1100 to 1886 |
|   |   | 2070 to 2280 |
| 3 | 6 | 1100 to 1886 |
|   |   | 2070 to 2244 |
| 4 | 5 | 1100 to 1392 |
|   |   | 1466 to 1830 |
|   |   | 2070 to 2118 |
| 5 | 16 | 1100 to 1392 |
|   |   | 1518 to 1780 |

For those skilled in the art of analyzing near-IR spectra of aqueous solutions having small analytical signals, the calibration exemplifies several well-known phenomena. It is generally known that signal, noise and pathlength considerations often dictate that the signal-rich combination band spectral region from, 2000 to 2500 nm be excluded from multivariate analyses that include the first overtone region from 1450 to 1900 nm. Many additional factors are required to fully model the smaller and more overlapped analytical signals in the first overtone region, with the result that the combination band spectral region from 2000 to 2500 nm would be over-modeled were it to be included. Such limitation is dictated by traditional multivariate methods that require a single number of factors for the entire spectral region being analyzed. Thus, the inventive PCR algorithm allows signal in a noisy region such as the combination band to be analyzed at the same time as signal in a more complex region like the first overtone. As the following discussion reveals, applying the inventive algorithm leads to smaller standard errors of prediction (SEP).

Figure 5:
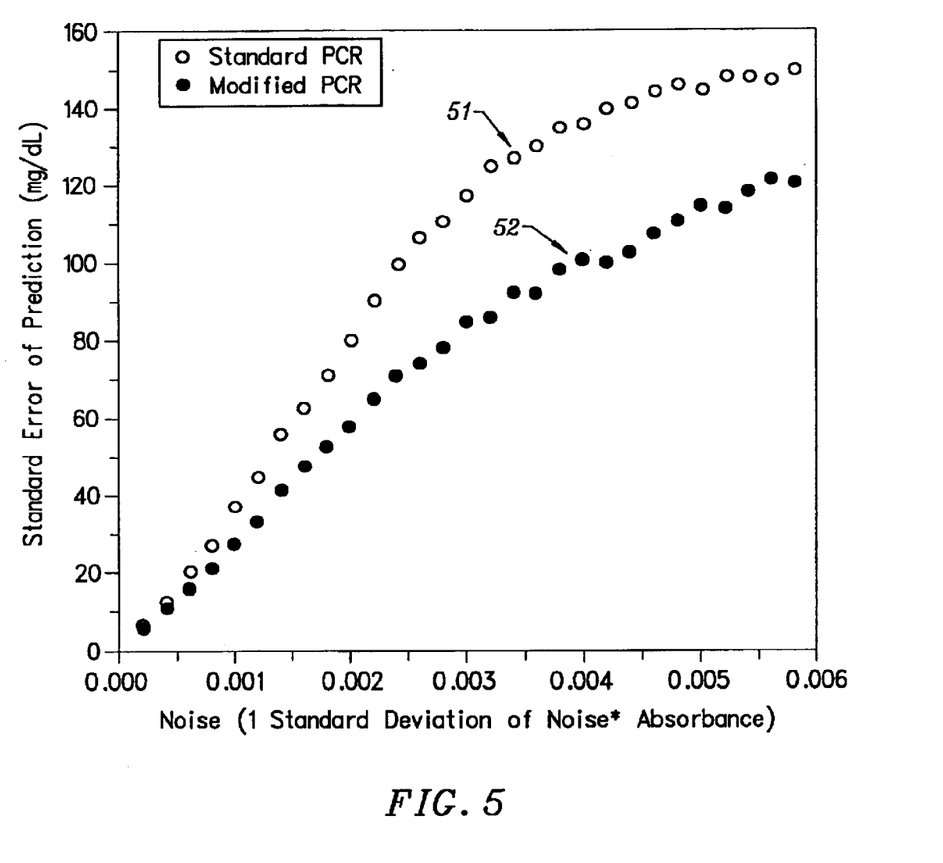
FIG. 5 plots SEP (Standard Error of Prediction) versus noise for Standard PCR and Modified PCR, according to the invention.
Figure 6:
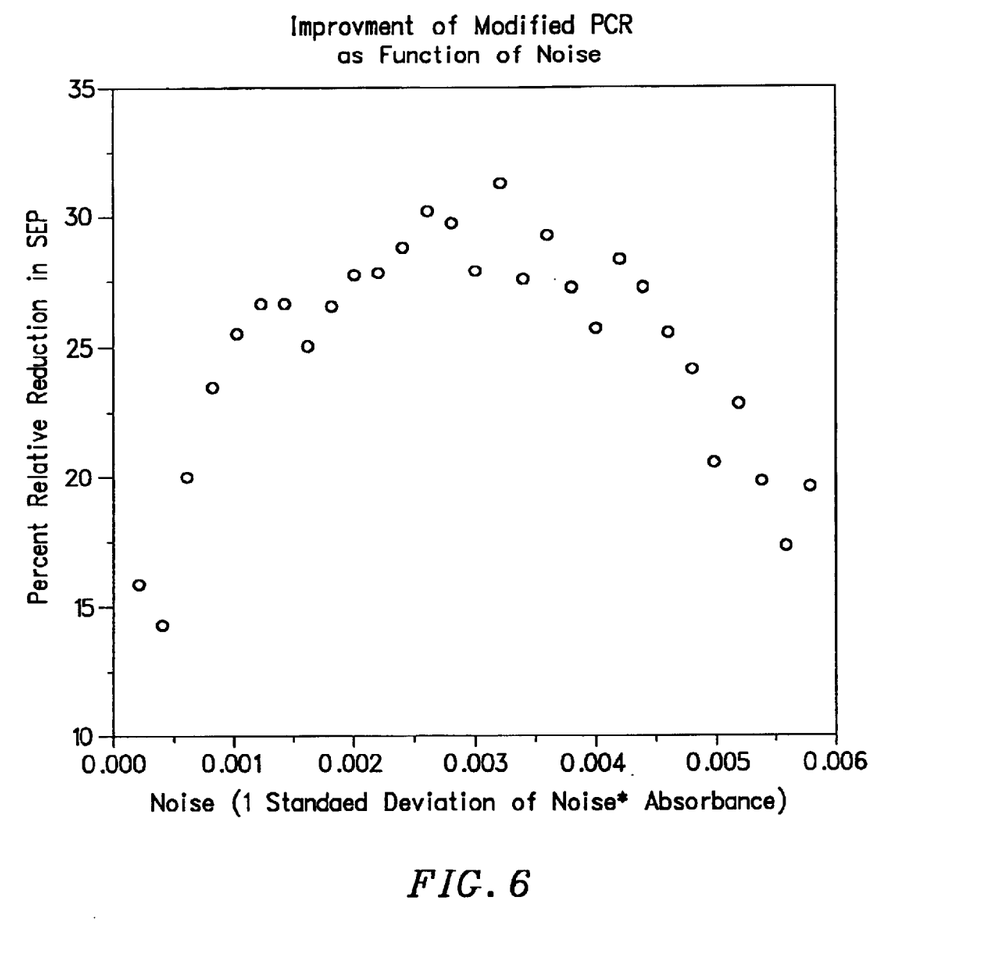
FIG. 6 plots the relative error level of Standard PCR and Modified PCR as a function of noise, according to the invention.

Predication: Using the calibrations developed with the conventional PCR algorithm and the inventive PCR algorithm, prediction results were obtained on the generated prediction sets. As previously indicated, in the prediction data sets, 50 sets of 80 spectra were generated at each of 30 noise levels from 0.0002 to 0.006 times the absorbance level. The mean SEP for the original PCR 51 and modified PCR algorithm 52 are presented in FIG. 5 for each of the noise levels tested. In all cases, the mean SEP of the modified PCR algorithm was lower than that of the standard PCR algorithm. In comparing the traditional PCR results to the modified PCR results, it is evident the reduction in the SEP ranged from 14 to 32% using the inventive PCR algorithm, as shown in FIG. 6. FIGS. 5 and 6 clearly show that the inventive PCR algorithm resulted in smaller prediction errors compared to the conventional PCR algorithm. At low noise levels where the spectral matrix and analytical signal is readily modeled, the two PCR approaches produce similar results. As well, at very high noise levels where no analytical signal is modeled (2 times the standard error approximating the mean of the analytical concentration) the two PCR approaches perform similarly.

Figure 7:
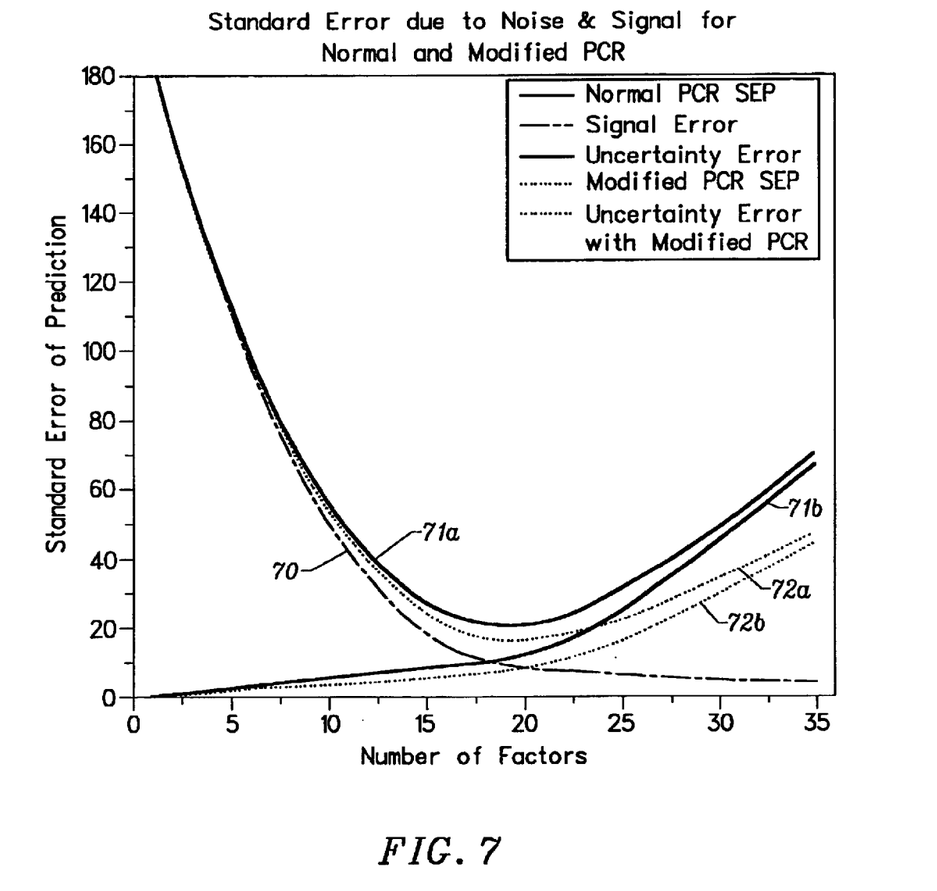
FIG. 7 plots SEP (standard error of prediction) and uncertainty error as a function of the number of factors used to model a signal, according to the invention.

The observed SEP versus the number of factors used to model the system classically decreases with initial factors to a local minimum and then increases slowly with additional factors. This is due to the calibration model modeling the analytical signal with early factors and increasingly modeling the spectral noise with later factors to the point of over-modeling the system. The observed SEP may be broken up into two components according to equation 2:

$$SEP = SE_{sig} + SE_{uncert} \quad (2)$$

where SEP is the standard error of prediction, $SE_{sig}$ is the standard error of the signal and $SE_{uncert}$ is the standard error due to the modeled uncertainty. If no noise or uncorrelated components of the sample were present in the model or in subsequent prediction spectra, the standard error of the modeled signal would continue to decrease with an increasing number of factors until the system was completely modeled as shown by the dashed and dotted line 70 in FIG. 7.

However, in generation of the calibration model both signal and uncertainty (noise) are modeled into the system. Additional factors increase the uncertainty modeled into the system. This results in the classical decrease in the SEP with early factors as the signal is modeled, a local minimum in the SEP and finally an increase in the SEP as the system is over-modeled with additional factors.

The cumulative removal of spectral regions that are fully modeled as in the inventive algorithm results in additional factors incorporating less uncertainty into the model as is represented by the dotted 72a,b versus solid 71a,b lines in FIG. 1. The modeled uncertainty thus does not increase as rapidly with additional factors. Since the SEP depends on the modeled signal as well as the modeled uncertainty, the resulting SE also decreases. Thus, the new algorithm provides a lower local minimum in the SEP with additional factors.

Other embodiments of the invention are possible. For example, the approach of PCR followed by wavelength selection with the subsequent residuals used as input for additional PCR models is readily extended to other multivariate techniques such as partial least squares (PLS). Additionally, residuals from one multivariate method may be used as inputs for another multivariate method.

The invention finds particular utility in various spectroscopy applications; for example, predicting concentration of analytes such as glucose from noninvasive near-IR spectra performed on live subjects. While the invention has been described herein with respect to near IR spectroscopy, the methods of the invention are equally applicable to data matrices of any kind. In the chemical arts, spectroscopic techniques may include UV/VIS/NIR/IR as well as techniques such as AA/NMR/MS. Furthermore, the invention is not limited to spectroscopic techniques but may include chromatographic techniques such as GC/LC or combinations of chromatographic and spectroscopic techniques such as GC/MS or GC/IR. Additionally, the invention finds application in almost any field that relies on multivariate analysis techniques, the social sciences, for example.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

What is claimed is:

1. A method of developing a calibration for predicting concentration of a target analyte in sample spectra, said method employing factor-based multivariate techniques, said method comprising the steps of:
   A. providing a matrix of calibration spectra;
   B. modeling at least one spectral region using a first selected number of factors;
   C. removing said modeled regions from said spectral matrix, so that, a residual matrix is generated;
   D. modeling at least one region of said residual matrix using a further selected number of factors, wherein said further selected number of factors may be equal to or different from said first selected number;
   E. repeating steps B through D, using said residual matrix as an input matrix for step B, until the number of factors employed for all iterations is equal to an optimal number of factors required to model at least a portion of said sample spectrum; and
   F. generating a vector of calibration coefficients wherein said vector constitutes said calibration;
   wherein a specific number of factors models at least one region of a spectrum independently of the number of factors used to model other spectral regions, thus minimizing prediction error.

2. The method of claim 1, wherein said multivariate techniques include Partial Least Squares (PLS) analysis.

3. The method of claim 1, wherein said multivariate techniques include Principal Component Regression (PCR).

4. The method of claim 3, wherein said factors are selected from a matrix of loading vectors and a matrix of scores, said matrix calibration spectra=$X_1$, said matrix of loading vectors=T, and said scores matrix=V, so that $$X_2 = TV^T,$$

and wherein using Principal Component Analysis (PCA) is employed to decompose $X_1$ to generate T, and wherein $X_1$ comprises I samples and k wavelengths.

5. The method of claim 4, wherein said scores matrix, V, is generated by PCA.

6. The method of claim 5, wherein the number of factors used in the current iteration=$x_n$, with z=the number of factors used for an iteration and n=the current iteration, so that said first number of factors=$z_1$; and wherein step B comprises the steps of:
   G. setting $T_n = T_u(:, 1:z_n)$; and
   H. setting $V_n = V_u(:, 1:z_n)$, where u=the number of factors in an optimal model.

7. The method of claim 6, wherein step C comprises the step of:
   I. calculating a residual spectral matrix $X_2$ from $X_1$ according to:

$$X_{n+1} = X_n - T_n V_n^T.$$

8. The method of claim 7, wherein step I further comprises the step of:
   J. eliminating at least one high-noise region from said residual spectral matrix.

9. The method of claim 8, wherein step J comprises the optional step of:
   K. calculating a mean residual spectrum according to:

$$Resi = \text{mean}(X_1 - T_1 V_1^T).$$

10. The method of claim 9, wherein step J further comprises any of the steps of:
    L. squaring said mean residual spectrum and removing at least one large value area; and
    M. removing at least one region where raw spectra have high absorbance, wherein noise is related to absorbance.

11. The method of claim 10, further comprising the step of:
    N. generating a final scores matrix by concatenating all previous scores matrices according to:

$$T_{all} = [T_1 Y_2 T_3 \ldots T_n].$$

12. The method of claim 11, wherein set F comprises:
    O. generating a vector of calibration coefficients, s, using multiple linear regression, wherein said vector s, constitutes said calibration, according to:

$$y = Ts, \text{ where y is a vector of i concentrations};$$

$$T^T y = T^T s;$$

$$(T^Y T)^{-1} T^T y = s; \text{ and}$$

$$S = (T^Y T)^{-1} y^T y.$$

13. The method of claim 1, wherein said prediction error is due to overmodeling of noisy spectral regions.

14. A method of predicting concentration of a target analyte from a prediction data set based on a multivariate calibration comprising steps of:
    A. providing a prediction data set, said prediction data set comprising a matrix of sample spectra;
    B. generating a calibration by modeling a calibration data set according to an iterative, combinative algorithm, wherein a specific number of factors models at least one region of a spectrum independently of the number of factors used to model other spectral regions; and
    C. applying said calibration to said prediction data set, so that a prediction of a target analyte concentration is produced;
    wherein prediction error is minimized.

15. The method of claim 14, wherein step B comprises steps of:
    D. modeling at least one spectral region from said calibration matrix using a first selected number of factors;
    E. subtracting said modeled regions from said calibration matrix, so that a residual matrix is generated;
    F. modeling at least one region from said residual matrix using a further selected number of factors, wherein said further selected number may be equal to or different from said first selected number;

G. repeating steps D through F, using said residual matrix as an input matrix for step B, until the number of factors employed for all iterations is equal to an optimal number of factors required to model at least a portion of said entire spectrum.

16. The method of claim 15, wherein said factors are selected from a matrix of loading vectors and a matrix of scores, said matrix calibration spectra=$X_1$, said matrix of loading vectors=T, and said-scores matrix=V, so that $$X_1 = TV^T,$$

and wherein using Principal Component Analysis (PCA) is employed to decompose $X_1$ to generate V, and wherein $X_1$ comprises i samples and k wavelengths.

17. The method of claim 16, wherein said scores matrix, T, is generated by regressing said matrix of loading vectors, V.

18. The method of claim 17, wherein the number of factors used in the current iteration=$Z_n$, with n=the current iteration and z=the number of factors used in an iteration, and wherein step E comprises the steps of:

H. setting $T_n = T_u(:, 1: Z_n)$; and
I. setting $V_n = V_u(:, 1: Z_n)$; where u=the number of factors in an optimal model.

19. The method of claim 18, wherein step E comprises the step of:

J. calculating a residual spectral matrix $X_2$ from $X_1$ according to:

$$X_{n+1} = X_n - T_n V_n^T.$$

20. The method of claim 19, wherein step E further comprises the step of:

K. eliminating at least one high-noise region from said residual spectral matrix.

21. The method of claim 20, wherein step K comprises the optional step of:

L. Calculating a mean residual spectrum according to:

$$Resi = \text{mean}(X_n - T_n V_n^T).$$

22. The method of claim 21, wherein step K comprises any of the steps of:

M. squaring said mean residual spectrum and removing at least one large value area; and
N. removing at least one region where raw spectra have high absorbance, wherein noise is related to absorbance.

23. The method of claim 22, further comprising the step of,

O. generating a final scores matrix by concatenating all previous scores matrices according to:

$$T_{all} = [T_1 T_2 T_3 \ldots T_s].$$

24. The method of claim 23, further comprising the step of:

P. generating a vector of calibration coefficients, s, using multiple linear regression, wherein said vector s, constitutes said calibration model, according to:

$y=Ts$, where y is a vector of 'I' concentrations;

$T^T y = T^T s;$ $(T^T T)^{-1} T^T y - s;$ and $s = (T^T T)^{-1} T^T y.$

25. The method of claim 24, wherein stop C comprises the steps of:

Q. generating a scores matrix $T'_1$ for said matrix of sample spectra, where said sample matrix=X', according to:

$$T'_1 = X' V_1;$$

R. computing a residual matrix for said sample matrix according to:

$$X'_1 = X' - T'_1 V_1^T;$$

S. removing at least one high noise region from said residual of said sample matrix;
T. repeating steps R through T, using said residual of said sample matrix with said high noise regions removed as an input matrix for step R, until a total number of factors employed for all iterations is equal to the said optimal number of factors employed for said calibration set.

26. The method of claim 25, wherein step C further comprises the step of:

U. generating a final scores matrix, $T_{all}$, for said samples matrix by concatenating all previous scores matrices according to:

$$T_{all} = [T'_1 T'_2 T'_3 \ldots T''_{1V}].$$

27. The method of claim 26, wherein step C further comprises the step of:

V. predicting concentration of said target analyte, $Y_{pred}$, according to:

$$y_{pred} = (T'_{all})s.$$

28. The method of claim 14, wherein said algorithm comprising an iterative, combinative PCR algorithm.

29. The method of claim 14, wherein said algorithm comprises an iterative, combinative PLS algorithm.

30. The method of claim 14, wherein said prediction error is due to overmodeling of noisy spectral regions.

31. An iterative, combinative algorithm for modeling a set of data, said algorithm comprising the steps of.

A. providing a data matrix containing an analytical signal, said data matrix comprising a plurality of samples and a plurality of variables;
B. modeling at least one region of said data matrix, a region constituting at least one of said plurality of values, using a selected number of factors;
C. subtracting said modeled regions from said data matrix, so that a residual matrix is generated;
D. modeling at least one further region from said residual matrix after removal of a further selected number of values, wherein said further selected number equal to or different from said first number; and
E. repeating steps B through D, using said residual matrix as an input matrix for step B, until the number of factors employed for all iterations is equal to an optimal number of factors required to model said entire data set; wherein a specific number of factors models at least one region of said data matrix independently of the number of factors used to model other regions of said data matrix so that said analytical signal is modeled.

32. The algorithm of claim 31, wherein said factors are selected from a matrix of loading vectors and a matrix of scores, said data matrix of =$X_1$, said matrix of loading vectors=T, and said scores matrix=V, so that $$X_1 = TV^T,$$

and wherein using Principal Component Analysis (PCA) is employed to decompose $X_1$ to generate V, and wherein $X_1$ comprises i samples and k variables.

33. The algorithm of claim 32, wherein said scores matrix, V, is generated by regressing said matrix of loading vectors, T.

34. The algorithm of claim 33, wherein the number of factors used in the current iteration=$z_n$, with z=the number of factors used in an iteration, and n=the current iteration, so that said first number of factors=$z_1$, and wherein step B comprises the steps of:
F. setting $T_n=T_u(:, 1: z_n)$; and
G. setting $V_n=V_u(:, 1: z_n)$, where u=the number of factors in an optimal model.

35. The algorithm of claim 34, wherein step C comprises the step of:
H. calculating a residual matrix $X_2$ from $X_1$ according to:

$$X_{n+z}=X_n\_T_nV_n^T.$$

36. The algorithm of claim 35, wherein step H further comprises the step of:
I. eliminating at least one high-noise region from said residual matrix.

37. The algorithm of claim 36, wherein step I comprises the optional step of:
J. calculating a mean residual matrix according to:

$$Resi=mean(X_n\_T_nV_n^T).$$

38. The algorithm of claim 37, wherein step I further comprises the step of:.
K. squaring said mean residual matrix and removing at least one large value region.

39. The algorithm of claim 37, further comprising the step of:
L. generating a final scores matrix by concatenating all previous scores matrices according to:

$$T_{all}=[T_1T_2T_3 \ldots T_s].$$

40. The algorithm of claim 39, further comprising the step of:
M. generating a vector of calibration coefficients, s, using Multiple Linear regression, wherein said vectors, s, constitutes a calibration, according to:
y=Ts, where y is a vector of l known values related to a predetermined parameter within said data set, said data set constituting a calibration data set;

$$T^Ty=s;$$
$$(T^TT)^{-1}T^Ty=s; \text{ and}$$
$$S=(T^TT)^{-1}T^Ty.$$

41. The algorithm of claim 40, further comprising the step of:
N. applying said calibration to a prediction data set, said prediction data set constituting a matrix, wherein actual values for said predetermined parameter are unknown, to generate a vector, $y_{pred}$, of predicted values for said parameter.

42. The algorithm of claim 41, wherein step N comprises the steps of:
O. generating a scores matrix $T'_1$ for said matrix of prediction data, where said matrix of prediction data= X', according to:

$$T'_1=X'V_1;$$

P. computing a residual matrix for said matrix X' according to:

$$X'_1=X'\_T_1V_1^T;$$

Q. removing at least one high noise region from said residual of said matrix X'; and
R. repeating steps O through Q, using said generated residual with said high noise regions removed as an input matrix for step V, until a total number of factors employed for all iterations is equal to the said optimal number of factors employed for said calibration set.

43. The a algorithm of claim 42, wherein step N further comprises the step of:
S. generating a final scores matrix, $T'_{all}$, for said prediction data set by concatenating all previous scores matrices according to:

$$T'_{all}=[T'_1T'_2T'_3 \ldots T'_s].$$

44. The algorithm of claim 43, wherein step N further comprises the step of:
T. generating said vector, $Y_{pred}$, according to:

$$y_{pred}=(T'_{all})s.$$

45. The method of claim 31, wherein overmodeling of noisy regions present in said data matrix is minimized.

46. The method of claim 31, wherein said analytical signal comprises a spectroscopic signal.

* * * * *